United States Patent [19]

Schriewer et al.

[11] Patent Number: 4,870,182

[45] Date of Patent: * Sep. 26, 1989

[54] 4-HYDROXY-QUINOLINE-3-CARBOXYLIC

[75] Inventors: Michael Schriewer; Klaus Grohe, both of Odenthal, Fed. Rep. of Germany

[73] Assignee: Bayer Aktiengesellschaft, Leverkusen, Fed. Rep. of Germany

[ * ] Notice: The portion of the term of this patent subsequent to Aug. 9, 2005 has been disclaimed.

[21] Appl. No.: 189,559

[22] Filed: May 3, 1988

Related U.S. Application Data

[60] Division of Ser. No. 43,663, Apr. 28, 1987, Pat. No. 4,804,760, and a continuation-in-part of Ser. No. 795,056, Nov. 5, 1985, Pat. No. 4,762,844.

[30] Foreign Application Priority Data

May 10, 1986 [DE] Fed. Rep. of Germany ....... 3615767

[51] Int. Cl.$^4$ ................ C07D 215/56; C07D 215/36; C07D 215/38; C07D 215/40
[52] U.S. Cl. .................................... 546/156; 560/23; 560/39
[58] Field of Search ............................... 546/153, 156

[56] References Cited

U.S. PATENT DOCUMENTS

| | | | |
|---|---|---|---|
| 4,380,632 | 4/1983 | Steffen | 546/156 |
| 4,552,882 | 11/1985 | Esteve-Soler | 546/156 |
| 4,665,079 | 5/1987 | Culbertson et al. | 514/312 |
| 4,762,844 | 8/1988 | Grohe et al. | 546/156 |
| 4,782,156 | 11/1988 | Grohe | 546/153 |

FOREIGN PATENT DOCUMENTS

| | | | |
|---|---|---|---|
| 230295 | 7/1987 | European Pat. Off. | |
| 235762 | 9/1987 | European Pat. Off. | 546/156 |
| 201869 | 9/1987 | Japan | 546/156 |

OTHER PUBLICATIONS

Sanchez et al., *J. Med. Chem.*, 31, p. 983, (1988).

*Primary Examiner*—Donald G. Daus
*Assistant Examiner*—E. Bernhardt
*Attorney, Agent, or Firm*—Sprung Horn Kramer & Woods

[57] ABSTRACT

A process for the preparation of a compound of the formula

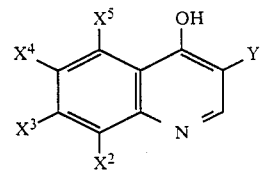

in which
Y is a nitrile group, an ester group COOR$^1$ or an acid amide CONR$^2$R$^3$,
R$^1$, R$^2$ and R$^3$ each independently is hydrogen or C$_1$–C$_4$-alkyl, and R$^3$ may also be phenyl, and
X$^2$, X$^3$, X$^4$ and X$^5$ each independently is hydrogen, halogen, nitro, cyano, alkyl having 1–3 carbon atoms, alkoxy having 1–3 carbon atoms, alkylmercapto having 1–3 carbon atoms, alkylsulphonyl having 1–3 carbon atoms, or a phenylsulphonyl group which is optionally substituted in the aryl radical, comprising reacting an aminoacrylate of the formula
in which
X$^1$ is halogen, a nitro group, an alkoxy, alkoxy, alkylmercapto or alkylsulphonyl group having 1–3 carbon atoms in each case, or an arylsulphonyl group,
W is hydrogen or a —CH$_2$CH$_2$Z radical,
Z is a nitrile group, an ester group COOR$^4$ or an acid amide group CONR$^5$R$^6$, and
R$^4$, R$^5$ and R$^6$ each independently is hydrogen or C$_1$–C$_4$-alkyl, and R$^5$ may also be phenyl, with an acid acceptor in an aprotic solvent. Some of the reactants are new, as are the products which are intermediates for antibacterially active 1-alkyl-4-quinolone-3-carboxylic acids.

3 Claims, No Drawings

4-HYDROXY-QUINOLINE-3-CARBOXYLIC

This is a division of application Ser. No. 043,663, filed Apr. 28, 1987, now U.S. Pat. No. 4,804,760 and a continuation-in-part of application Ser. No. 795,056, filed Nov. 5, 1985, now U.S. Pat. No. 4,762,844.

The invention relates to a new process for the preparation of 4-hydroxy-quinoline-3-carboxylic acids. These compounds are important intermediates, particularly for the preparation of antibacterially active 1-alkyl-4-quinolone-3-carboxylic acids.

The preparation of 4-hydroxy-quinoline-3-carboxylic acids is known (Prog. Drug Research 21 (1977), 9).

They are obtained when appropriately substituted anilines are reacted with alkoxymethylene malonates and the primary adduct is cyclized by heating either in polyphosphoric acid or in diphenyl ether.

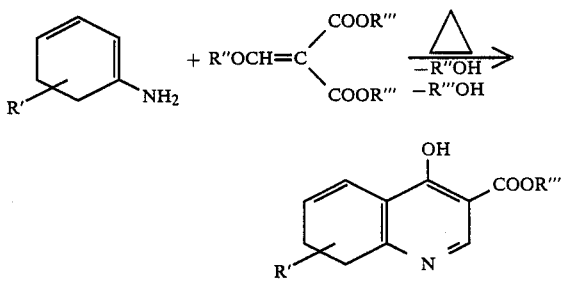

However, this process has some significant disadvantages:
(1) High reaction temperatures are necessary. This is particularly disadvantageous in the case of thermally labile substituents.
(2) Depending on the substitution on the aniline, a mixture of isomeric quinolines can be expected.
(3) Anilines having electron-withdrawing substituents react poorly.

In contrast to this, the process according to the invention leads, under mild conditions and in good yields, to isomerically pure 4-hydroxy-quinoline-3-carboxylic acids. Accordingly, compounds of the formula I

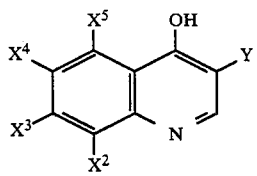

in which

Y represents a nitrile group, an ester group $COOR^1$ or an acid amide $CONR^2R^3$, where $R^1$, $R^2$ and $R^3$ represent hydrogen of $C_1-C_4$-alkyl, and $R^3$ may be phenyl, if appropriate, and $X^2$, $X^3$, $X^4$ and $X^5$ represent hydrogen, halogen, nitro, cyano, alkyl having 1–3 carbon atoms, alkoxy having 1–3 carbon atoms in the alkyl radical, alkylmercapto having 1–3 carbon atoms in the alkyl radical, alkylsulphonyl having 1–3 carbon atoms in the alkyl radical, and also a phenylsulphonyl group which is optionally substituted in the aryl radical,
can be obtained when aminoacrylates of the formula II

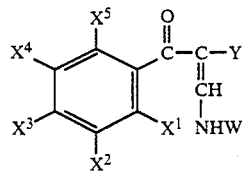

in which

Y, $X^2$, $X^3$, $X^4$ and $X^5$ have the abovementioned meaning and $X^1$ denotes halogen, preferably fluorine or chlorine, a nitro group, an alkoxy, alkylmercapto or alkylsulphonyl group having 1–3 carbon atoms in each case, and also an arylsulphonyl group, and W represents hydrogen or a $-CH_2CH_2Z$ radical, where Z represents a nitrile group, an ester group $COOR^4$ or an acid amide group $CONR^5R^6$, where the radicals $R^4$, $R^5$ and $R^6$ represent hydrogen or $C_1-C_4$-alkyl, and $R^6$ may be phenyl, if appropriate, are reacted in an aprotic solvent in the presence of a base.

It is here to be described as surprising that, in the case of $W=-CH_2CH_2Z$, the cyclization of II and the elimination of the auxiliary group $CH_2=CHZ$ proceeds with formation of I in a so-called one-pot reaction.

The enamines II required as starting materials for the process according to the invention can be obtained by reaction of the enol ethers of the formula III

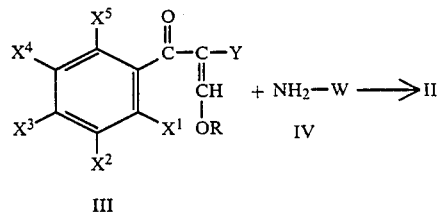

in which $X^1-X^5$ and Y have the specified meaning, with amines of the formula IV, in which W has the abovementioned meaning.

The enol ethers III are known or may be prepared according to the following general reaction scheme:

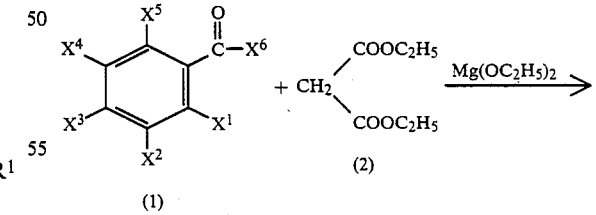

(1)

$X^6$ = Cl, Br, F

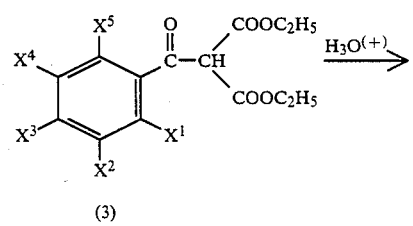

(3)

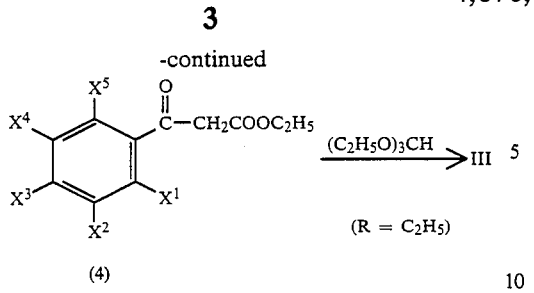

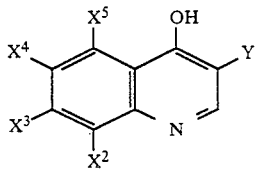

Accordingly, diethyl malonate (2) is acrylated in the presence of magnesium ethylate using the appropriate benzoyl halide (1) to form the acyl malonate (3) (Organicum, 3rd edition 1964, p. 438).

By means of partial saponification and decarboxylation of (3) in aqueous medium with catalytic amounts of sulphuric acid or 4-toluenesulphonic acid, the ethyl benzoylacetate (4), which is converted into ethyl 2-benzoyl-3-ethoxy-acrylate (III $R = C_2H_5$) using triethyl orthoformate/acetic anhydride, is obtained in good yield. The reaction of (III) with the amines (IV) in a solvent such as, for example, methylene chloride, an alcohol, chloroform, cyclohexane or toluene leads, in a slightly exothermic reaction, to the desired intermediates (II).

The cyclization reactions (II)→(I) are carried out in a temperature range from about 60°–300° C., preferably 80°–180° C.

As diluent, dioxane, dimethyl sulphoxide, N-methylpyrrolidone, sulpholane, hexamethylphosphoric triamide and, preferably, N,N-dimethylformamide may be used.

The cyclocondensations may be carried out at atmospheric pressure, but also at increased pressure. In general, the reactions are carried out at pressures between about 1 and about 100 bar, preferably 1 and 10 bar.

Suitable acid acceptors for the cyclization reactions (II)→(I) are potassium tert.-butanolate, 1,4-diaza-bicyclo[2,2,2]-octane (DABCO), 1,8-diaza-bicyclo[5,4,0]undec-7-ene (DBU), butyl-lithium, phenyl-lithium, phenyl-magnesium bromide, sodium methylate, sodium ethylate, sodium hydride, and sodium or potassium carbonate. Potassium or sodium fluoride become particularly preferred when hydrogen fluoride has to be eliminated.

For the cyclization (II)→(I), two equivalents of base are required in the case of W = hydrogen and one equivalent of base is required in the case of $W = CH_2CHZ$. It can be advantageous to employ an excess of 10 mol-% of base in each case.

The benzoyl halides (1) used as starting materials for this synthetic route are known. The following may be mentioned as examples: 2,3,4,5-tetrafluorobenzoyl chloride, pentafluorobenzoyl chloride, 2,4-dichloro-5-fluorobenzoyl chloride, 2,4-dichlorobenzoyl chloride, 2-chloro-5-fluorobenzoyl chloride, 2-chloro-5-fluorobenzoyl chloride, 2-chloro-4-methyl-benzoyl chloride, 2,4,5-trifluorobenzoyl fluoride, 2,5-dichlorobenzoyl fluoride, 2,3,4,5-tetrachlorobenzoyl chloride and 4-nitro-2-chloro-benzoyl chloride.

The amines of the formula IV used as starting materials for this synthetic route are known. The following may be mentioned as examples:

Ammonia, 3-aminopropionitrile, ethyl 3-aminopropionate, dimethyl 3-aminopropionamide and 3-aminopropionanilide.

The invention furthermore relates to 4-hydroxy-3-quniolinecarboxylic acid derivatives of the formula I

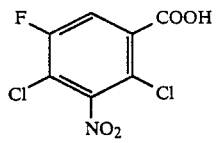

in which

Y and $X^5$ have the abovementioned meaning, and $X^2$ represents nitro, cyano, an alkyl, alkoxy, alkylmercapto or alkylsulphonyl group, in each case having 1–3 carbon atoms in the alkyl part, and also a phenylsulphonyl group which is optionally substituted in the aryl radical, and $X^3$ and $X^4$ represent nitro and halogen, particularly chlorine and fluorine.

The invention likewise relates to compounds of the formula I in which

Y, $X^2$, $X^3$, $X^4$ and $X^5$ have the abovementioned meaning and $X^2$, $X^3$, $X^4$ and $X^5$ may additionally represent amino.

These compounds can be obtained from the corresponding nitro derivatives by reduction methods which are known from the literature.

The following examples describe the invention:

EXAMPLE 1

Ethyl 2-(2,4-dichloro-5-fluoro-3-nitro-benzoyl)-3-ethoxyacrylate (a) 2,4-Dichloro-5-fluoro-3-nitro-benzoic acid

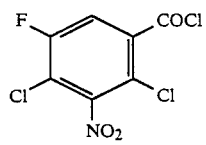

40 ml of concentrated nitric acid are added dropwise to 34 ml of concentrated sulphuric acid with ice cooling and stirring. 20.9 g of 2,4-dichloro-5-fluorobenzoic acid are introduced in portions into this nitration mixture, the temperature rising to 45°–50° C. The mixture is then heated at 90°–100° C. for a further 3 hours, cooled to room temperature and poured into 350 ml of ice water, and the precipitate is filtered off under suction and washed with water. The moist crude product is dissolved in 30 ml of hot methanol, and 150 ml of $H_2O$ are added to the solution. The cold precipitate is filtered off under suction, washed with $CH_3OH/H_2O$ and dried at 80° C. in vacuo. 21.2 g of crude 2,4-dichloro-5-fluoro-3-nitro-benzoic acid are obtained. It is adequately pure for the further reactions. A sample, recrystallized from toluene/petroleum ether, yields crystals of melting point 192° C.

(b) 2,4-Dichloro-5-fluoro-3-nitro-benzoyl chloride 106.6 g of 2,4-dichloro-5-fluoro-3-nitro-benzoic acid are refluxed with 250 ml of thionyl chloride for 2 hours. The excess thionyl chloride is then removed by distillation at atmospheric pressure and the residue is fractionated in a high vacuum. 104.7 g of 2,4-dichloro-5-fluoro-3-nitro-benzoyl chloride pass over at 110°–115° C./0.08–0.09 mbar. On standing, crystals of melting point 35°–37° C. form.

(c) Ethyl (2,4-dichloro-5-fluoro-3-nitro-benzoyl)-acetate

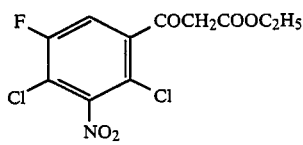

2.1 g of tetrachloromethane are added to 10.1 g of magnesium turnings in 21 ml of ethanol, and a mixture of 66.6 g of diethyl malonate, 40 ml of ethanol and 150 ml of toluene are added dropwise at 50°–60° C. after the commencement of hydrogen evolution. The mixture is stirred for 1 hour at this temperature, cooled to $-5°--10°$ C., and a solution of 109.2 g of 2,4-dichloro-5-fluoro-3-nitro-benzoyl chloride in 50 ml of toluene is slowly added dropwise. The mixture is then stirred for 1 hour at 0° C., brought to room temperature overnight, and warmed at 40°–50° C. for a further 2 hours. A mixture of 160 ml of water and 10.4 ml of concentrated sulphuric acid are added to the reaction mixture with ice cooling, and the organic phase is separated off. The aqueous phase is extracted with toluene, and the combined organic extract is washed with saturated sodium chloride solution and dried with sodium sulphate, and the solvent is stripped off. 144.5 g of diethyl(2,4-dichloro-5-fluoro-3-nitro-benzoyl)malonate are obtained as a crude product. After addition of 200 ml of water and 0.6 g of 4-toluenesulphonic acid, this is refluxed for 3 hours, the mixture is extracted with methylene chloride, the extract is dried using sodium sulphate, and the solvent is removed by distillation in vacuo. 118 g of substituted benzoylacetate are obtained as a crude product. It has adequate purity for the further reactions.

(d) Ethyl 2-(2,4-dichloro-5-fluoro-3-nitro-benzoyl)-3-ethoxy-acrylate

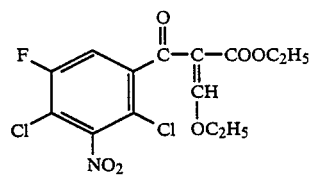

244.8 g of ethyl(2,4-dichloro-5-fluoro-3-nitrobenzoyl)-acetate are heated at 150°–160° C. with 166 g of triethyl orthoformate and 185 g of acetic anhydride for 3 hours. The mixture is then concentrated in vacuo and 270 g of ethyl 2-(2,4-dichloro-5-fluoro-3-nitrobenzoyl)-3-ethoxy-acrylate are obtained as an oily residue.

EXAMPLE 2

Ethyl 2-(2,4-dichloro-5-fluoro-3-methylbenzoyl)-3-ethoxyacrylate (a) 2,4-Dichloro-3-methyl-5-nitrobenzoic acid 30 g of 2,4-dichloro-3-methylbenzoic acid are initially introduced into 83 ml of concentrated $H_2SO_4$. 16.7 g of $KNO_3$ are added in portions with ice cooling. The mixture is subsequently warmed at 50° C. for a further 2 hours and then poured onto ice. The nitro compound is isolated and recrystallized from toluene. Melting point 152°–4° C., yield: 24 g.

(b) 5-Amino-2,4-dichloro-3-methylbenzoic acid 55 g of 2,4-dichloro-3-methyl-5-nitrobenzoic acid and 141.6 g of $Na_2S_2O_4$ are boiled for 3 hours in a mixture of 440 ml of a glycol monomethyl ether and 440 ml of water. 620 ml of ½ concentrated HCl are added to the still warm solution, which is then re-boiled. After cooling to room temperature, the mixture is poured into 1.5 liters of water, and the pH is adjusted to 5 using soda. 24.6 g of aminobenzoic acic are obtained. Melting point 202°–3° C.

(c) Methyl 5-amino-2,4-dichloro-3-methylbenzoate 24 g of 5-amino-2,4-dichloro-3-methylbenzoic acid are initially introduced into 100 ml of methanol. HCl gas is passed in for 20 minutes, and the mixture is subsequently refluxed for 5 hours. The mixture is then poured into water and rendered alkaline using soda. 24 g of ester of melting point 86°–88° C. are obtained.

(d) 2,4-Dichloro-5-fluoro-3-methylbenzoic acid 24 g of methyl 5-amino-2,4-dichloro-3-methyl-benzoate are diazotized in aqueous solution using NaNO₂/HCl. 26 ml of 30% strength aqueous $HBF_4$ solution at 0° C. are added to the diazonium salt solution. The reaction mixture is maintained at 0° C. for 30 minutes. The tetrafluoroborate is then isolated and dried over $P_2O_5$. Yield 23.5 g.

68 g of this tetrafluoroborate are thermally decomposed in o-dichlorobenzene. After work-up, 15 g of methyl 2,4-dichloro-5-fluoro-3-methylbenzoate of boiling point 139°–40° C. (16 mbar) are obtained.

12.8 g of this ester are boiled for 1½ hours with 4 g of NaOH in 100 ml of ethanol/water. After cooling, the mixture is acidified with HCl and filtered under suction. 12 g of the title compound are obtained. Melting point 167°–69° C.

(e) Ethyl (2,4-dichloro-5-fluoro-3-methyl-benzoyl)acetate 3 ml of ethanol and 0.5 ml of carbon tetrachloride are added to 1.4 g of magnesium turnings. After initiation of the reaction, a mixture of 8.7 g of diethyl malonate, 6 ml of ethanol and 23 ml of toluene are added at 50° C. The mixture is warmed for 1 hour at 50°–60° C. and then cooled to $-5°--10°$ C. A solution of 13.3 g of 2,4-dichloro-5-fluoro-3-methylbenzoyl chloride (from 2,4-dichloro-5-fluoro-3-methylbenzoic acid and thionyl chloride) in 6 ml of toluene is added dropwise at this temperature. The mixture is then allowed to come to room temperature. After standing overnight, a mixture of 24 ml of water and 4 ml of $H_2SO_4$ is added. The phases are separated, and the organic phase is washed with water, dried and concentrated. 20 ml of water and 0.1 g of p-toluenesulphonic acid are added to the oily residue. The mixture is refluxed for 4.5 hours, the phases are subsequently separated, and the organic phase is dried and concentrated in vacuo. 14.1 g of the titled compound remain as a crude oil.

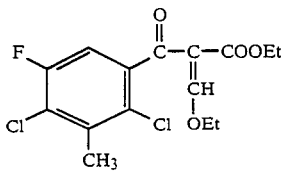

(f) Ethyl 2-(2,4-dichloro-5-fluoro-3-methyl-benzoyl)-3-ethoxy-acrylate 14.1 g of the compound from (e), 10.7 g of ethyl orthoformate and 12.3 g of acetic anhydride are boiled for 2 hours. The volatile components are then removed by distillation first in a water-pump vacuum and then in a high vacuum at a bath temperature of 130° C. 14 g of the title compound remain (oil).

EXAMPLE 3

Ethyl 2-(2,4-difluoro-3-methyl-benzoyl)-3-ethoxyacrylate (a)

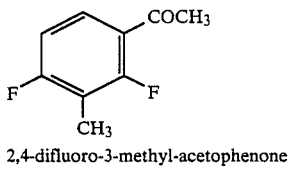

2,4-difluoro-3-methyl-acetophenone

First 24.6 g of acetyl chloride and subsequently 38.5 g of 2,6-difluorotoluene are added dropwise to a suspension of 48 g of AlCl₃ in 120 ml of 1,2-dichloroethane under cooling. The mixture is then stirred for 2.5 hours at 50° C. The reaction mixture is subsequently poured onto ice, the phases are separated, and the aqueous phase is extracted with 1,2-dichloroethane. The combined organic phases are washed with NaOH and water, dried over $K_2CO_3$ and concentrated. The residue is distilled under reduced pressure. Boiling point: 90°–93° C. (10 torr), Yield: 42.9 g.

(b)

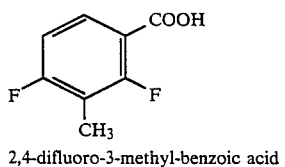

2,4-difluoro-3-methyl-benzoic acid

A solution of 30 g of 2,4-difluoro-3-methylacetophenone in 270 ml of dioxane is added dropwise with ice cooling to a bromine lye prepared from 72 g of NaOH, 86.4 g of bromine and 360 ml of water, at 10° C. The mixture is allowed to come to room temperature, a further 80 ml of water are added, and the phases are separated. A solution of 18 g of $Na_2S_2O_5$ in 270 ml of water is added to the aqueous phase. The mixture is then acidified using HCl, the acid precipitating. Yield 24.9 g of 2,4-difluoro-3-methylbenzoic acid. Melting point: 180°–81° C.

(c) Ethyl(2,4-difluoro-3-methyl-benzoyl)-acetate

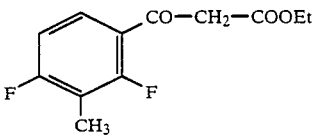

8 ml of ethanol and 1 ml of carbon tetrachloride are added to 3.6 g of magnesium turnings. After initiation of the reaction, a mixture of 22.2 g of ethyl malonate, 15 ml of ethanol and 60 ml of toluene are added at 50° C. The mixture is warmed for 1 hour at 50°–60° C. and then cooled to −5°−−10° C. A solution of 25.7 g of 2,4-difluoro-3-methyl-benzoyl chloride (from 2,4-difluoro-3-methylbenzoic acid and thionyl chloride) in 15 ml of toluene is added dropwise at this temperature. The mixture is then allowed to come to room temperature. After standing overnight, a mixture of 60 ml of water and 10 ml of $H_2SO_4$ is added dropwise. The phases are separated, and the organic phase is washed with water, dried and concentrated. 50 ml of water and 0.2 g of p-toluenesulfonic acid are added to the oily residue. The mixture is refluxed for 4.5 hours, the phases are separated, and the organic phase is dried and concentrated in vacuo. 33.9 g of the title compound remain as a crude oil.

(d) Ethyl 2-(2,4-difluoro-3-methyl-benzoyl)-3-ethoxyacrylate

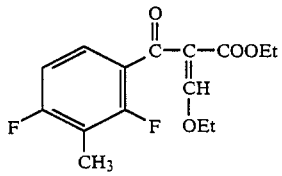

33.9 g of the crude ethyl(2,4-difluoro-3-methylbenzoyl)-acetate, 32 g of ethyl orthoformate and 36 g of acetic anhydride are heated for 2 hours at 150° C. A distillation is then carried out, first in a waterpump vacuum and then in a high vacuum at a bath temperature of 130° C. 30.7 g of the title compound remain (oil).

EXAMPLE 4

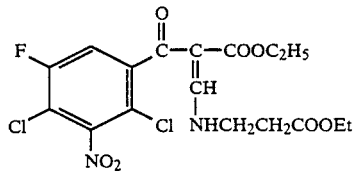

Ethyl 2-(2,4-dichloro-5-fluoro-3-nitro-benzoyl)-3-(2-ethoxycarbonylethylamino)-acrylate.

38 g of ethoxy acrylate from Example 1 are initially introduced into 150 ml of methylene chloride. An aqueous solution of 15.4 g of ethyl 3-aminopropionate hydrochloride is added to this. A solution of 8.4 g of $NaHCO_3$ in water is added dropwise to the two-phase system with vigorous stirring. After completion of the dropwise addition, the mixture is stirred for a further 2 hours, and the phases are subsequently separated. The organic phase is washed with water, dried over $Na_2SO_4$, and concentrated. The solid residue is slurried in diethyl ether and subsequently isolated. Yield: 38 g, melting point 107°–8° C.

EXAMPLE 5

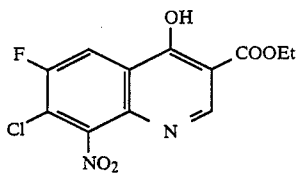

Ethyl 7-chloro-6-fluoro-4-hydroxy-8-nitro-3-quinoline-carboxylate 52 g of the product from Example 4 and 18.5 g of K$_2$CO$_3$ are heated at 140° C. for 4 hours in 160 ml of DMF. The mixture is subsequently poured onto ice and acidified, and the precipitated solid is isolated. It is dried and recrystallized from glycol methyl ether acetate. Yield: 35.8 g, melting point: 226°–8° C. (decomposes).

EXAMPLE 6

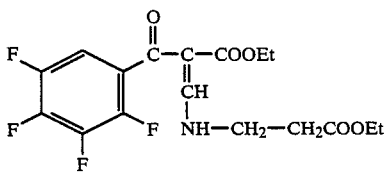

Ethyl 3-(2-ethoxycarbonyl-ethylamino)-2-(2,3,4,5-tetrafluoro-benzoyl)acrylate 6.4 g of ethyl 3-ethoxy-2-(2,3,4,5-tetrafluoro-benzoyl)acrylate are initially introduced into 30 ml of methylene chloride. A solution of 3.1 g of ethyl 3-amino-propionate hydrochloride in 12 ml of water is added to this. A solution of 1.7 g of NaHCO$_3$ in 20 ml of water is added dropwise to the two-phase mixture with vigorous stirring. After the dropwise addition is complete, the mixture is stirred for a further 3 hours. The phases are then separated, and the organic phase is washed with water and dried over Na$_2$SO$_4$. After concentration, 7.8 g of the title compound remain. Melting point: 96°–97° C.

EXAMPLE 7

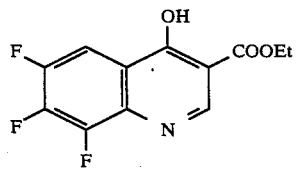

Ethyl 6,7,8-trifluoro-4-hydroxy-3-quinolinecarboxylate 7.7 g of the compound from Example 6 and 2.9 g of K$_2$CO$_3$ are heated at 140°–5° C. for 4 hours in 36 ml of DMF. The mixture is subsequently poured onto ice and acidified, and the precipitated solid is separated off and dried. Yield: 4.5 g, melting point: 279°–82° C.

EXAMPLE 8

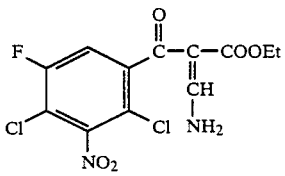

Ethyl 3-amino-2-(2,4-dichloro-5-fluoro-3-nitro-benzoyl)acrylate 38 g of the product from Example 1 are initially introduced into 40 ml of ethanol. A mixture of 8 ml of concentrated NH$_3$ solution in 25 ml of ethanol is added dropwise with ice cooling. The mixture is stirred for 2 hours at room temperature and the phases are then separated. The organic phase is washed with water and dried. 38.3 g of the title compound remain on concentration. Melting point: 113°–114° C.

EXAMPLE 9

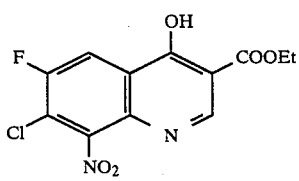

Ethyl 7-chloro-6-fluoro-4-hydroxy-8-nitro-3-quinolinecarboxylate 7.0 g of the product from Example 8 are initially introduced into 100 ml of dioxane. 4.7 g of potassium tert.-butylate are added to this in portions. The mixture is stirred for 24 hours at room temperature, poured onto ice, and neutralized. The precipitated solid is isolated and dried. Yield: 5.3 g, melting point: 224°–7° (decomposes)

EXAMPLE 10

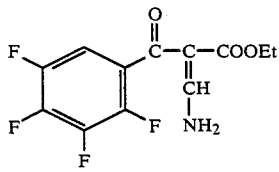

Ethyl 3-amino-2-(2,3,4,5-tetrafluoro-benzoyl)-acrylate 12.8 g of ethyl 3-ethoxy-2-(2,3,4,5-tetrafluoro-benzoyl)-acrylate are initially introduced into 16 ml of EtOH. A mixture of 3.3 ml of concentrated aqueous NH$_3$ solution and 10 ml of EtOH is added dropwise with ice cooling. The mixture is subsequently stirred for 2 hours. Ice-water is then added, and the precipitated solid is filtered off under suction. Yield: 8.7 g, melting point: 118°–119° C.

EXAMPLE 11

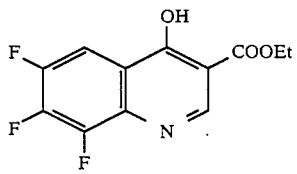

Ethyl 6,7,8-trifluoro-4-hydroxy-3-quinoline-carboxylate 5.8 g of the product from Example 10 are initially introduced into 25 ml of dioxane. 4.8 g of potassium tert.-butylate are added in portions at room temperature.

The temperature of the reaction mixture increases during this addition. The mixture is stirred for 24 hours, then poured onto ice and rendered acid. The solid is isolated, dried and recrystallized from glycol monomethyl ether/ethanol. Yield: 3.1 g, melting point 278° C.

EXAMPLE 12

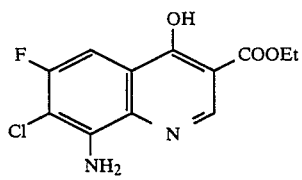

Ethyl 8-amino-7-chloro-6-fluoro-4-hydroxy-3-quinolinecarboxylate 9.4 g of the product from Example 5 and 19.2 g of iron turnings are warmed at 80° C. for 1 hour in 190 ml of acetic acid. The mixture is then heated briefly to 110° C. and filtered while hot. Ice-water is then added to the filtrate, and the precipitated solid is isolated. After drying at 110° C., the product is recrystallized from glycol monomethyl ether. Yield: 7.8 g, melting point: 268°–70° C.

It will be understood that the specification and examples are illustrative but not limitative of the present invention and that other embodiments within the spirit and scope of the invention will suggest themselves to those skilled in the art.

I claim:

1. A 4-hydroxy-3-quinolinecarboxylic acid derivative of the formula

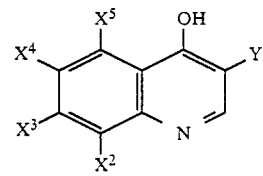

in which

Y is a nitrile group, an ester group $COOR^1$ or an acid amide $CONR^2R^3$, $R^1$, $R^2$ and $R^3$ each independently is hydrogen or $C_1$–$C_4$-alkyl, and $R^3$ may also be phenyl, $X^5$ is hydrogen, halogen nitro, amino, cyano, $C_1$–$C_3$-alkyl, $C_1$–$C_3$-alkoxy, $C_1$–$C_3$-alkylmercapto, $C_1$–$C_3$-alkylsulphonyl, or phenyl sulphonyl group, $X^2$ is nitro, amino, cyano, an alkyl, alkoxy, alkylmercapto or alkylsulphonyl group in each case having 1–3 carbon atoms, or phenylsulphonyl group, and $X^3$ and $X^4$ each independently is nitro, amino or halogen.

2. A compound according to claim 1, in which $X^5$ is hydrogen, halogen nitro, cyano, $C_1$–$C_3$-alkyl, $C_1$–$C_3$-alkoxy, $C_1$–$C_3$-alkylmercapto, $C_1$–$C_3$-alkylsulphonyl, or phenyl sulphonyl group, $X^2$ is nitro, amino, cyano, an alkyl, alkoxy, alkylmercapto or alkylsulphonyl group in each case having 1–3 carbon atoms, or phenylsulphonyl group, and $X^3$ and $X^4$ each independently is nitro, chlorine or fluorine.

3. A compound from the group consisting of

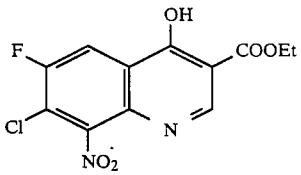

and

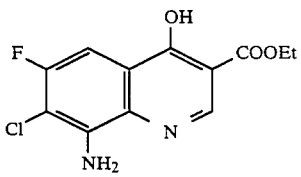

* * * * *